United States Patent [19]

Coburn

[11] Patent Number: 5,396,440
[45] Date of Patent: Mar. 7, 1995

[54] OPTIMUM CALIBRATION FREQUENCY DETERMINATION

[75] Inventor: Joel T. Coburn, Midland, Mich.

[73] Assignee: The Dow Chemical Company, Midland, Mich.

[21] Appl. No.: 273,583

[22] Filed: Jul. 11, 1994

Related U.S. Application Data

[63] Continuation of Ser. No. 3,165, Jan. 12, 1993, abandoned.

[51] Int. Cl.$^6$ ............................................. G06F 15/20
[52] U.S. Cl. ........................... 364/571.02; 364/571.01; 356/346
[58] Field of Search ................... 364/497, 489, 571.02, 364/571.01; 356/126, 124, 127, 346

[56] References Cited

U.S. PATENT DOCUMENTS

| | | | |
|---|---|---|---|
| 3,960,497 | 6/1976 | Acord | 23/253 |
| 4,744,657 | 5/1988 | Aralis et al. | 356/319 |
| 4,779,216 | 10/1988 | Collins | 364/571.02 |
| 4,866,644 | 9/1989 | Shenk et al. | 364/571.02 |
| 4,893,253 | 1/1990 | Lodder | 364/497 |
| 4,916,645 | 4/1990 | Wuest et al. | 364/571.04 |
| 4,927,269 | 5/1990 | Keens et al. | 356/346 |
| 4,969,993 | 11/1990 | Nahs, Jr. et al. | 210/198.2 |

OTHER PUBLICATIONS

E. A. Yfantis, et al., "Optimum Frequency of Calibration Monitoring", *Chemometrics and Intelligent Laboratory Systems*, vol. 3, pp. 39–43 (1988).

H. C. Smit, "The Use of Kalman Filtering and Correlation Techniques in Analytical Calibration Procedures" *Jnal. of Research of the Nat'l Bureau of Standards*, vol. 90, No. 6, pp. 441–450, (1985).

*Primary Examiner*—Emanuel T. Voeltz
*Assistant Examiner*—Kamini S. Shah
*Attorney, Agent, or Firm*—James T. Hoppe

[57] ABSTRACT

One aspect of the invention is a method for determining whether systematic biases are present in an instrument. The method involves first obtaining a series of replicates produced by an instrument. Then, a Fourier Transform is performed on that data, thereby generating a secondary spectrum which indicates the frequency characteristics of the data. This secondary spectrum is then compared to secondary spectra obtained in a similar matter from a series of random number sets to determine whether variations observed are within an expected range as defined by the random number series.

Another aspect of the invention is a method for determining an optimum frequency at which the instrument should be calibrated. This method comprises obtaining a set of multivariate data as before, and treating every xth data point as a calibration point and adjusting the values of the points following the calibration point accordingly. A Fourier Transform is then calculated as before. Different values for x are tried, and an optimum calibration frequency is deemed to be a value for x in a region which produces a point which is most similar to the distribution of points corresponding to the series of random number sets.

16 Claims, 4 Drawing Sheets

OPTIMUM CALIBRATION FREQUENCY DETERMINATION

CROSS-REFERENCE TO RELATED APPLICATION

This is a continuation of application Ser. No. 08/003,165, filed Jan. 12, 1993, now abandoned.

This invention relates to the recognition of biases in instruments and to the determination of the optimum frequency at which an instrument should be calibrated. More particularly this invention concerns using a Fourier Transform to generate information on the frequency characteristics of an instrument and comparing these frequency characteristics to frequency characteristics obtained using random number sequences.

BACKGROUND OF THE INVENTION

Analytical instruments are used extensively in production as well as in research settings. The quality of the process or research depends in large part on the accuracy and precision of the analytical instrument. Unfortunately many of these instruments are prone to drifting and other forms of systematic biases. To counteract this, analytical instruments are periodically recalibrated using a known standard. The biases present in a particular instrument are not always linear, however. Thus, simply recalibrating the instrument more often will not always result in a more accurate analysis. Furthermore, the cost of the analysis in time and money increases with increasing rates of calibration, and so it is not always cost effective to increase the frequency of calibrations even when slightly more accurate results could be obtained. Accordingly it is desirable to be able to identify and characterize the systematic biases in a particular instrument so that an optimum calibration frequency can be determined.

One method of determining the optimum recalibration period is described by Walter Ligget, in "Tests of the Recalibration Period of a Drifting Instrument", National Bureau of Standards, Gaithersburg, Md. 20899. The method described by Ligget assumes a linear model to characterize the dependence of drift with time. Instruments whose responses oscillate do not correlate closely with a linear model, making this method inappropriate for some applications. Furthermore, the method described by Ligget only uses the upper half of a Fourier Transform to determine whether the instrument response is random by determining spectral flatness. The lower half of the transform is not used as the method requires that the spectrum be tapered to eliminate biases due to low frequency variations. The method also requires that outliers and linear trends be identified and removed before the spectral flatness is determined. These requirements reduce the versatility of the method and eliminate possibly relevant data from consideration.

Another method was described by H. C. Smit in the *Journal of Research of the National Bureau of Standards*, 90, 441–450, (1985). This method, like the method described by Ligget, assumes a linear model to describe the dependence of drift with time. Therefore this method also suffers from some of the same disadvantages as the method described by Ligget. Specifically, this method is not satisfactory for use in instruments where the response oscillates over time.

OBJECTS OF THE INVENTION

It is therefore an object of the present invention to provide a method for identifying systematic biases in an instrument so that the operator can be alerted to the need for periodic recalibration.

It is a further object of the invention to provide a method for determining a frequency at which an analytical instrument should be recalibrated in order to maximize precision and accuracy of the instrument as well as minimizing the cost of the analysis.

SUMMARY OF THE INVENTION

These and other objects are achieved by the invention, one aspect of which is a method for determining whether biases are present in an analytical instrument. It was discovered that some instruments produce oscillating biases making determinations based on linear models inappropriate. Accordingly, a new method was devised.

The method generally comprises first obtaining a series of replicates produced by an instrument. The instrument can be anything which is capable of producing a set of multivariate data, such as in chromatography, spectroscopy, or any measuring devices. Then, a Fourier Transform is performed on that data, thereby generating a secondary spectrum which indicates the frequency characteristics of the data. A series of random number sets is then obtained, each set having a similar number of elements as the series of replicates. A Fourier Transform is then performed for each of the random number sets, thereby generating a series of secondary spectra which indicate the frequency characteristics of the random number sets.

The Fourier Transforms obtained for the random number sets are then compared with the Fourier Transform obtained from the set of replicates of multivariate data. Most preferably, this comparison is accomplished by first calculating the area under the first quarter and the first half of the Fourier Transform spectra generated for the set of multivariate data and for each of the random number sets. Next, values for the area under the first quarter of the spectra can be plotted against the values for the area under the first half of the spectra. The relationship between the point representing the set of multivariate data and the distribution of points representing the random number sets is an indication as to the randomness of the set of multivariate data.

Another aspect of the invention is a method for determining an optimum frequency at which the instrument should be calibrated. This method comprises obtaining a set of multivariate data as before, and treating every xth data point as a calibration point and adjusting the values of the points following the calibration point accordingly. A Fourier Transform is then calculated as before. Different values for x are tried, and the optimum calibration frequency is deemed to be the value for x which produces a point which is most similar to the distribution of points corresponding to the series of random number sets.

Additional advantages and features of the present invention will become apparent from a reading of the detailed description of a preferred embodiment which makes reference to the following set of drawings in which:

DETAILED DESCRIPTION OF THE INVENTION

Figure 1:
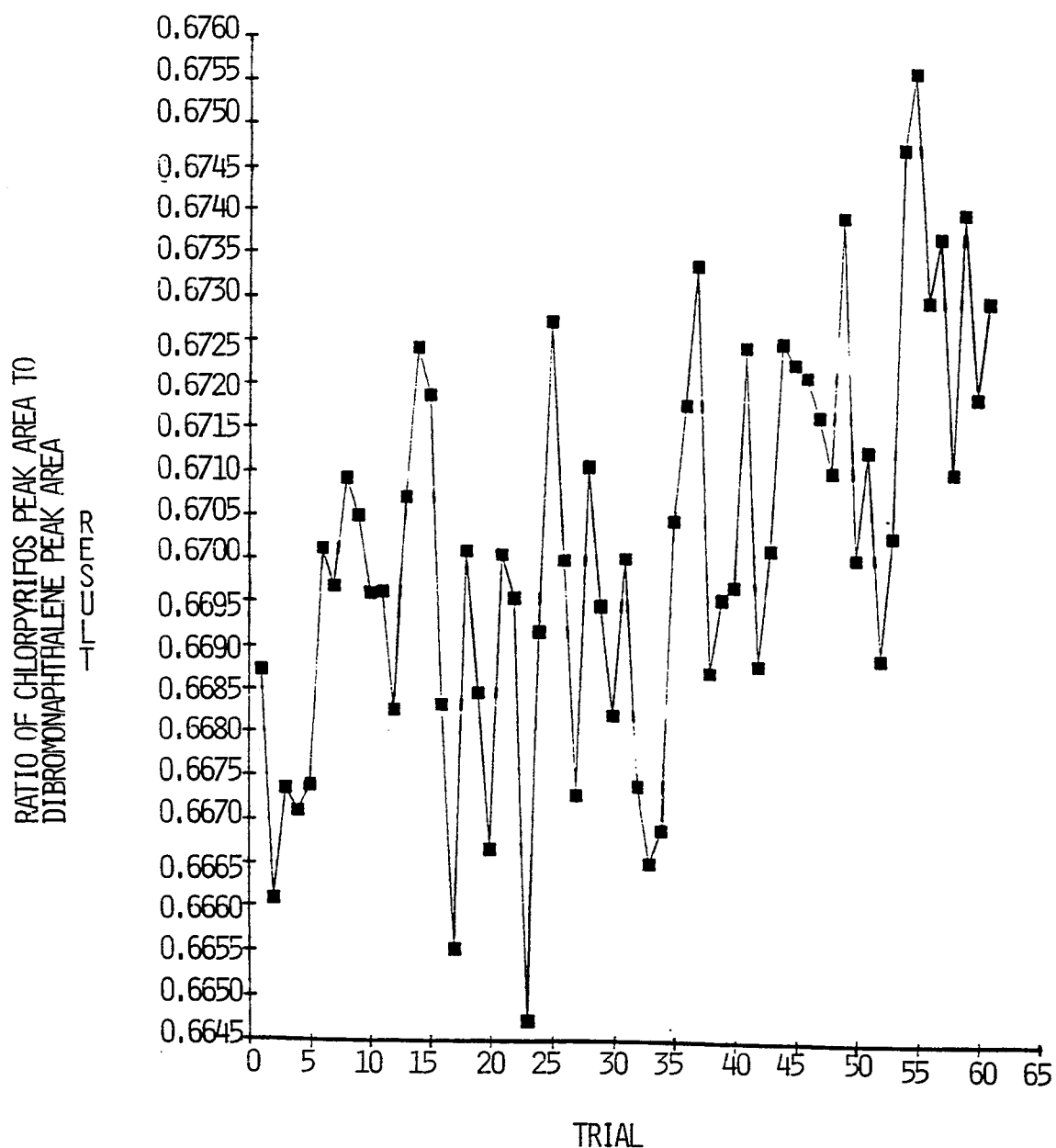
FIG. 1 is a run chart of the results from 61 liquid chromatography analyses of a single sample of chlorpyrifos with dibromonaphthalene as an internal standard.

The invention is a method for determining the time-dependent characteristics of an analytical instrument to detect systematic variability thereby allowing the determination of an optimum instrument calibration frequency. The method is suitable for any analytical instrument which can be used to generate multivariate data. This includes detectors commonly associated with chromatography or spectroscopy. This also includes measuring devices such as flowmeters and balances which need to be recalibrated periodically.

The first step in the method is to obtain an initial set of data consisting of a number of replicates from the same sample or a set of identical samples. Although the particular number of replicates is not important, a larger number of replicates generally provides more information about the instrument, and leads to more accurate calibration frequency determinations.

This data set is then treated as a waveform which has been sampled at a rate equal to the cycle time of a single analysis. A Fourier Transform is then performed on the data, the absolute values of which are used to produce a secondary spectrum. Although both the real and the imaginary numbers which make up the Fourier transform can be used to generate the secondary spectrum, satisfactory results are obtained when using only the real numbers. It is preferred that a Fast Fourier Transform be used to produce the secondary spectrum, although any other method of performing Fourier Transforms (such as a Discrete Fourier Transform) can also be used. For more specific information on how to carry out Fourier Transforms see W. Press, B. Flannery, S. Teukolsky and W. Vetterling, *Numerical Recipes: The Art of Scientific Computing*, Cambridge University Press, New York (1989), hereby incorporated by reference.

The shape of the secondary spectrum produced by the Fourier Transform is an indication as to whether the variations in the instrument are purely random or whether they are subject to some systematic error or biases. The higher the amplitude of the secondary spectra the better the correlation to the cosine wave having the indicated frequency. Completely random variations would not be expected to correlate with any particular frequency of cosine wave better than another and so would be expected to yield a spectrum with a flat amplitude distribution. Furthermore, since random variations would not be expected to correlate well with any cosine wave, it would be expected that the spectrum would have a relatively low value for the maximum amplitude observed. A set of data with systematic biases due to drift would be expected to correlate better with cosine waves of lower frequencies than with cosine waves of higher frequencies, however. This is because lower frequencies correspond to changes happening over longer periods of time such as from run to run whereas higher frequencies correspond to more rapid changes such as noise. Noise is typically a random phenomenon and so an instrument with a systematic bias would be expected to yield a secondary spectrum which has relatively larger amplitudes at lower frequencies and smaller amplitudes at higher frequencies.

In order to determine whether the secondary spectrum which corresponds to the set of replicates is within the expected range for random variations, a series of random number sets is obtained. These random numbers may be obtained from any source generally known in the art, including published tables and outputs from computers. Each random number set should contain a similar number of elements as there were replicates in the initial data set. The number of random number sets obtained depends on the needs of the particular analyses, with larger numbers of sets providing more reliable comparisons.

After the random number sets have been obtained, each set is subjected to a Fourier Transform. The absolute value of the Fourier Transform is then used to create a series of secondary spectra. Pattern Recognition techniques can then be used to compare this series of secondary spectra to the secondary spectra produced using the initial set of data. If the pattern recognition technique reveals that the secondary spectrum for the initial data set is not within the expected distribution of random variations, then periodic recalibration of the instrument is required for accurate results from the instrument.

In order to determine the correct frequency at which the instrument should be recalibrated, the initial set of replicates are used to simulate different patterns of re-calibration. Some of the points were assumed to have come from standard determinations while other points resulted from unknown samples. Every xth point in the initial set is treated as a standard and used as a calibration point, where x is an integer greater than one. The value obtained for a replicate deemed to be a calibration point is used to adjust the observed values for all of the points after that calibration point and before the next calibration point. When all of the values have been adjusted to reflect the periodic calibration, the Fourier transform is again performed.

Pattern recognition techniques are then used to compare the resulting secondary spectrum to the distribution of secondary spectra resulting from the random number sets. Different values for x are tried and a plot can be made of the value for x vs. the degree of closeness to the random number distributions. The optimum frequency at which to recalibrate the instrument is indicated by the calibration frequency which produced a secondary spectrum which was most similar to the set of secondary spectra generated from the set of random numbers. Thus, for optimum results, a standard should be run and the instrument recalibrated every xth analysis, where x is selected from the region of this plot containing the value for x which produces the least difference from the random number distribution. This value for x may or may not be the value which produces the absolute minimum Euclidean distance as consideration must also be given to the cost of more frequent calibrations.

Many different pattern recognition techniques are known (see e.g., C. Albano, W. Dunn, U. Edlund, E. Johansson, B. Nordén, M. Sjöström and S. Wold, *Analytica Chimica Acta*, Vol. 103, pp. 429–443 (1978)) and can be used with this invention. These techniques have been used to gain information concerning multivariate data. Further examples of pattern recognition techniques can be found in areas such as chemical structure analysis (see e.g., M. Sjöstroöm and U. Edlund, *Journal of Magnetic Resonance,* vol. 25, p. 285 (1977)).

For the determination of biases in an analytical instrument, the preferred pattern recognition technique comprises first calculating the areas under specific portions of the spectra. The ratio of these areas will then be compared to give an indication of the similarity of the initial set of data to the series of random numbers. As mentioned above, the amplitude of the secondary spectra is more important at the lower frequencies as this is the area where systematic biases will most likely show up. Thus, it is preferred that the area under initial portions of the secondary spectra (which corresponds to the lower frequencies) be used to determine the similarity. Most preferably, the areas under the first quarter and the first half of the spectra are calculated, although the specific fractions under which the area is measured is not critical.

A plot can then be constructed of the area under the first quarter vs. the area under the first half of each secondary spectrum. It should be understood that for the purposes of this disclosure, "plot" means a representation of the data in a coordinate system and therefore includes electronic methods where no physical graph is actually created. The distance between the center of the distribution of the points representing the random number sets and the point representing the initial data set is an indication of the randomness in the variation which occurs in the initial data set. This distance can be quantified by calculating the Euclidean distance which is given by the formula:

$$T = \left[ \left( \frac{AVG_{25} - AREA_{25}}{SD_{25}} \right)^2 + \left( \frac{AVG_{50} - AREA_{50}}{SD_{50}} \right)^2 \right]^{\frac{1}{2}}$$

where $AVG_{25}$, $AVG_{50}$, $SD_{25}$ and $SD_{50}$ are the average and standard deviations of the areas of the first quarter and first half of the secondary spectra obtained from the random distributions, and $AREA_{25}$ and $AREA_{50}$ are the areas of the first quarter and first half of the secondary spectra obtained from initial data set.

The invention will become more clearly understood by considering the following example which illustrates the invention.

EXAMPLE

The variability of a liquid chromatography instrument was analyzed as an example of the present invention. A sample of chlorpyrifos with dibromonaphthalene as an internal standard was prepared by weighing 0.16 grams of chlorpyrifos and 0.07 grams of dibromonaphthalene into 25 mL of 82% acetonitrile, 17.5% water and 0.5% acetic acid (v/v). This sample was analyzed 61 times by a liquid chromatography instrument which included a ZORBAX ODS 4.6 mm i.d., 25 cm length column with 5 micron particles and a KRATOS Spectroflow 783 detector. The chromatographic peak areas for chlorpyrifos and dibromonaphthalene were obtained and the ratio of the area of chlorpyrifos to dibromonaphthalene was calculated for each of the 61 analyses. These ratios appear as a run chart in FIG. 1.

Figure 2:
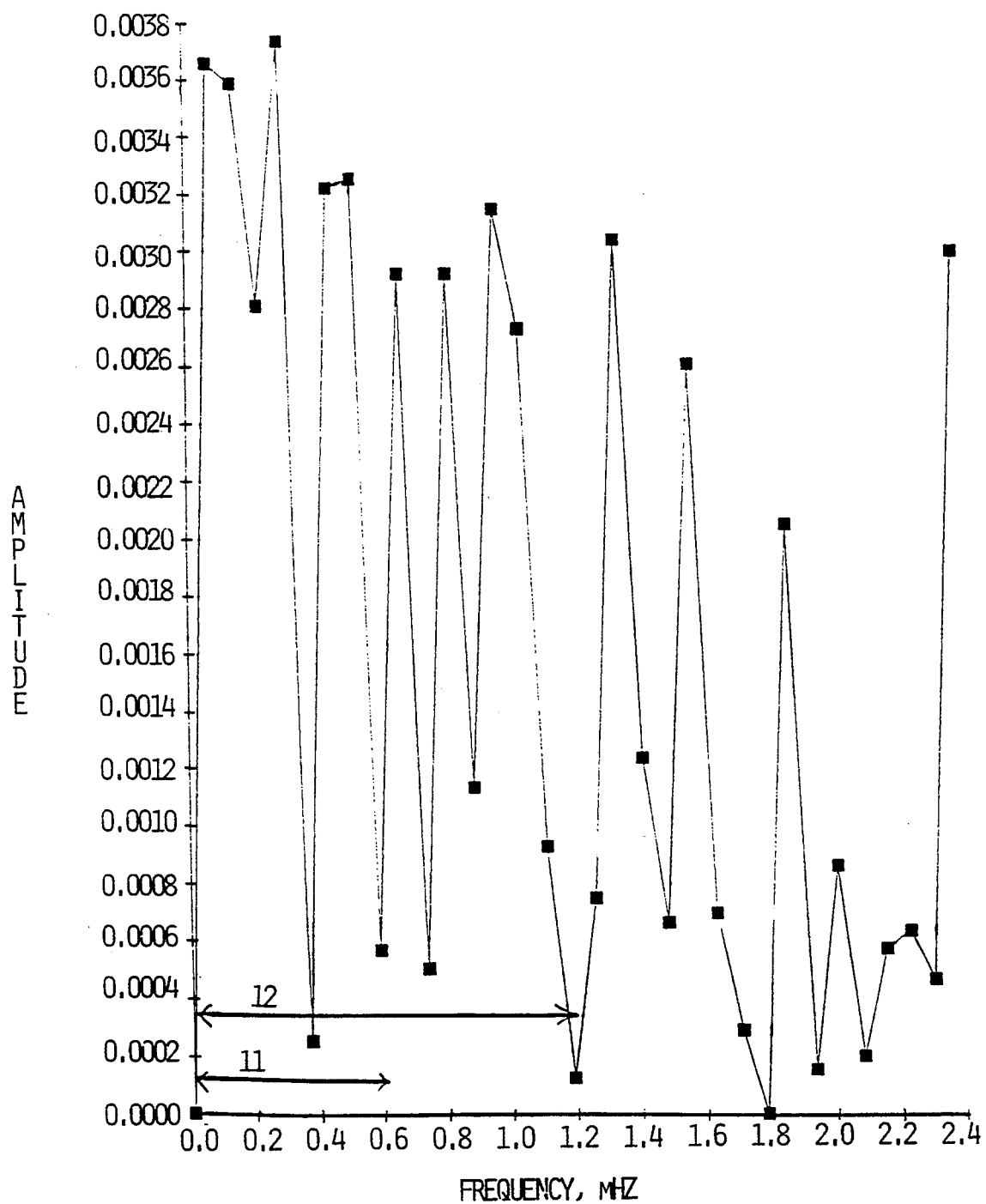
FIG. 2 is the spectrum which resulted from performing a Fast Fourier Transform on the data from FIG. 1.
Figure 3:
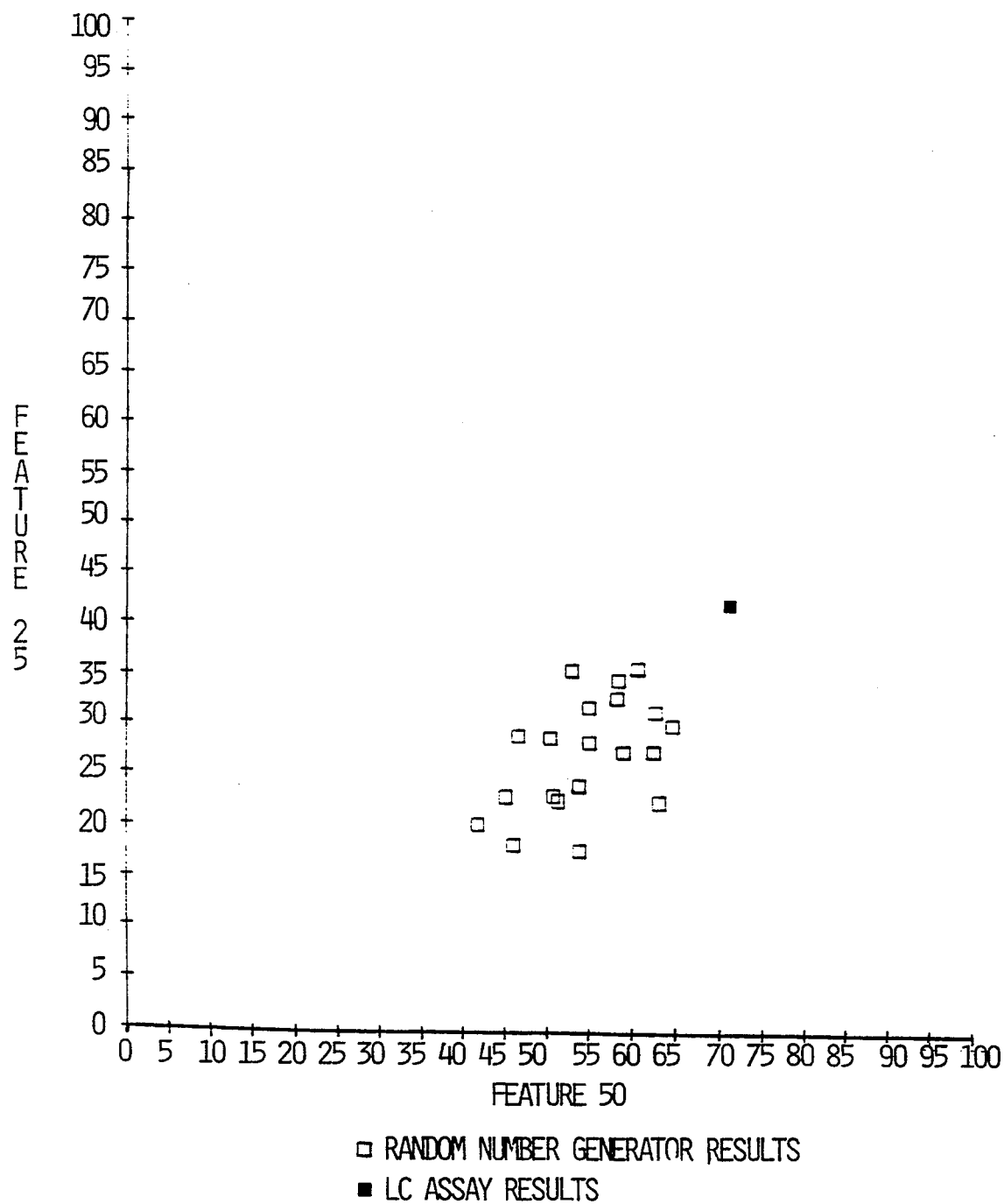
FIG. 3 is a plot of pattern recognition features for the spectrum of FIG. 2 and a series of 20 spectra which were generated using random numbers.

These points were then treated as a waveform which had been sampled at a rate equal to the cycle time of a single analysis. The data was then prepared for performing a Fast Fourier Transform by adding zeros so that the data string consisted of a number of entries which was an exact power of two. The Fast Fourier Transform was performed and the resulting secondary spectrum, shown in FIG. 2, was obtained by using the absolute values of the real part of the Fast Fourier Transform. The area under the first quarter of the spectrum (labelled 11 in FIG. 2) and the area under the first half of the spectrum (labelled 12) were then calculated. These areas were then plotted, as shown by the filled square in FIG. 3.

Next, a series of twenty random number sets, each containing 64 elements was generated. Each of these sets was subjected to a Fast Fourier Transform as above, producing 20 secondary spectra. The areas under the first quarter and first half were then calculated for each of the secondary spectra. These values were plotted and appear as the open squares in FIG. 3.

The distance between the center of the distribution of points corresponding to the random number sets and the point corresponding to the chlorpyrifos replicates is an indication of the randomness of the variability in the chlorpyrifos analysis. This was quantified by calculating the Euclidean distance or T-Distance according to the formula:

$$T = \left[ \left( \frac{AVG_{25} - AREA_{25}}{SD_{25}} \right)^2 + \left( \frac{AVG_{50} - AREA_{50}}{SD_{50}} \right)^2 \right]^{\frac{1}{2}}$$

where $AVG_{25}$, $AVG_{50}$, $SD_{25}$ and $SD_{50}$ are the average and standard deviations of the areas of the first quarter and first half of the secondary spectra obtained from the random distributions, and $AREA_{25}$ and $AREA_{50}$ are the areas of the first quarter and first half of the secondary spectra obtained from the initial chlorpyrifos data set. A T-value greater than three was deemed to be outside the region where random distributions reside. For this example the value for T was calculated to be 3.8 indicating that there was a systematic bias occurring over the course of the 61 assays. Therefore, periodic recalibration of this analytical instrument is required.

The same data string shown in FIG. 1 was then used to determine what the optimum calibration frequency is for this instrument. Various calibration sequences were simulated by assuming that some of the points in FIG. 1 were obtained from standard determinations and others from sample determinations. The calibration sequences were run in a regular fashion, for example, one standard-five samples-one standard-five samples, etc., which is a 1-5-1-5 sequence. Simulated calibrations were performed for sequences ranging from 1-1-1 to 1-9-1-9 with increasing numbers of samples between calibration. The calibration frequency or $C_f$ is defined as:

$$C_f = N_C/N_D$$

where $N_C$ is the number of calibrations and $N_D$ is the number of determinations in a sequence.

Figure 4:
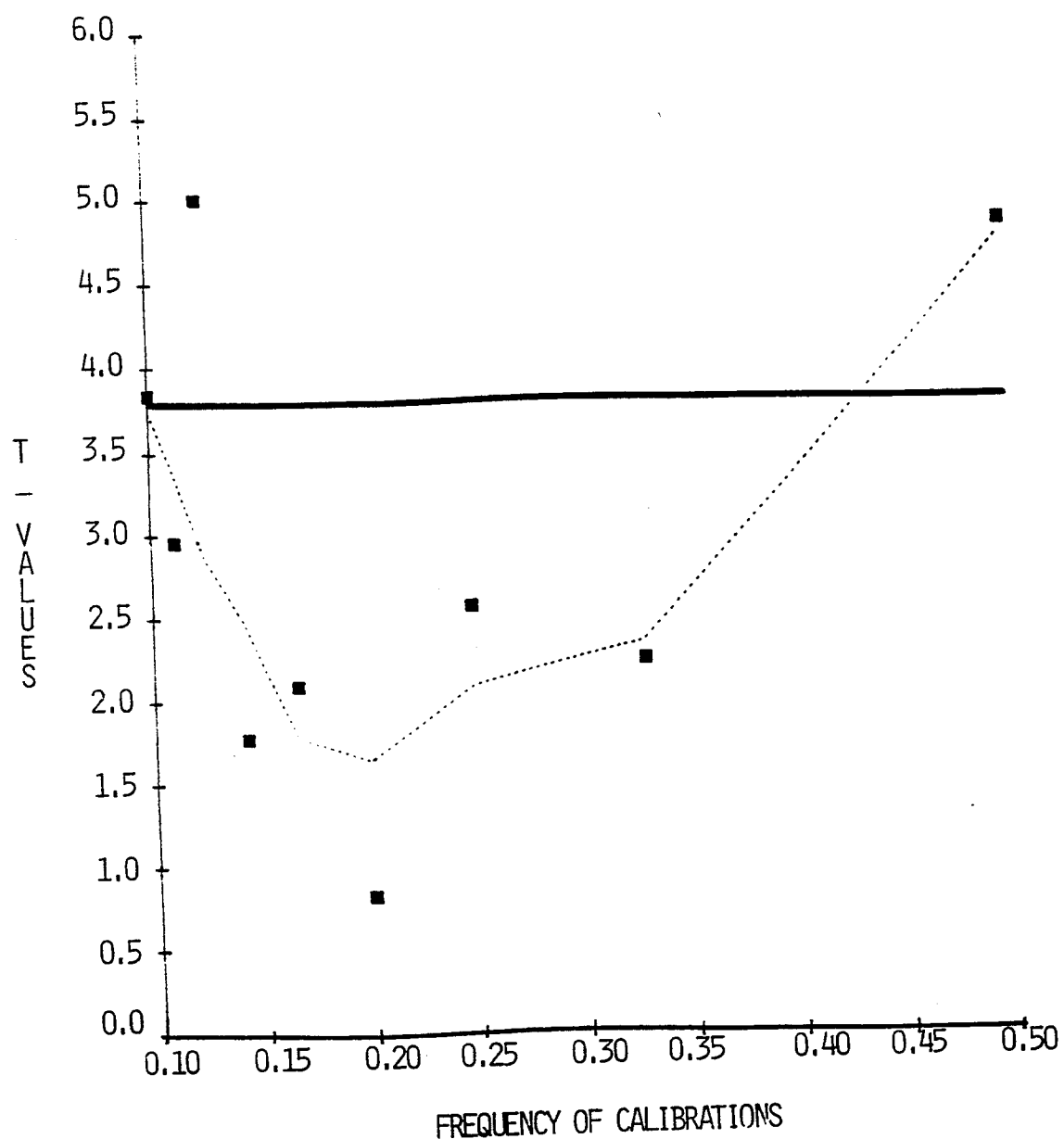
FIG. 4 is a plot of t-values obtained for different calibration frequencies.

Fourier Transforms were recalculated for each simulated calibration pattern, and the areas under the first quarter and the first half were again plotted. The Euclidean Distance or t-distance was then also recalculated. FIG. 4 depicts a plot of the T-Distance vs. the calibration frequency simulated. The calibration frequency which yielded the results which were most similar to the results of the random number sets is deemed to be the optimum calibration frequency. As seen from FIG. 2, a calibration frequency of 0.2 (or a 1-4-1-4 scheme) gave the lowest value for the T-distance and is therefore the optimum calibration frequency. It is interesting to note that a calibration frequency of 0.5 (or recalibrating the instrument after each "analysis") gave poor results indicating that the bias is not linear.

In order to get an indication of the improvement in accuracy the invention provides, it was assumed that the data string in FIG. 1 was calibrated according to the first data point and no more calibrations performed. The remaining 60 points were averaged and compared to the calibration point revealing an average systematic error of 0.5%. Then it was assumed that every 5th point was a calibration point as this was determined to be the optimum calibration frequency. Thus, points 2–4 were averaged and compared to point one, points 6–9 were averaged and compared to point 5, etc. This resulted in an average systematic error of only 0.09% or a five-fold reduction in error.

It should be realized by one of ordinary skill in the art that the invention is not limited to the exact configuration or methods illustrated above, but that various changes and modifications may be made without departing from the spirit and scope of the invention as described within the following claims.

What is claimed is:

1. A method for evaluating a sample comprising:
   using an analytical instrument selected from the group consisting of chromatography, spectroscopy, flowmeters and balances to measure a physical property of the sample;
   correlating the physical property measured using the analytical instrument with results obtained from analyzing standards having known properties under similar conditions;
   periodically determining whether biases are present in the analytical instrument; and
   recalibrating the analytical instrument and reanalyzing the sample if biases are determined;
   wherein the step of determining whether biases are present comprises:
   (a) obtaining a set of multivariate data generated by the analytical instrument;
   (b) performing a Fourier Transform for the data in step (a) thereby generating a spectrum which indicates the frequency characteristics of the data;
   (c) obtaining a series of random number sets having a similar number of elements to the set of multivariate data obtained in step (a);
   (d) performing a Fourier Transform for each of the random number sets in step (c) thereby generating a series of spectra which indicate the frequency characteristics of the random number sets; and
   (e) identifying biases in the instrument whenever the Fourier Transforms obtained in step (b) are not within the expected range of random distributions given the Fourier Transforms obtained in step (d).

2. The method of claim 1 wherein step (e) comprises:
   (f) calculating the area under a first portion of the spectral widths generated in steps (b) and (d);
   (g) calculating the area under a second portion of the spectral widths generated in steps (b) and (d);
   (h) plotting the values obtained in step (f) against the values obtained in step (g) for each random set and for the set of multivariate data;
   (i) ascertaining the distance the point representing the set of multivariate data is from the center of the distribution of random number sets; and
   (j) determining whether the distance determined in step (i) is within a range of values determined to be normal given the distribution of the points representing the random number sets.

3. The method of claim 2 wherein the first portion in step (f) is the first quarter of the spectral widths and the second portion in step (g) is the first half of the spectral widths.

4. The method of claim 3 wherein step (j) comprises calculating the Euclidean distance according to the formula:

$$T = \left[ \left( \frac{AVG_{25} - AREA_{25}}{SD_{25}} \right)^2 + \left( \frac{AVG_{50} - AREA_{50}}{SD_{50}} \right)^2 \right]^{\frac{1}{2}}$$

and where a T value of three or more is deemed to be indicative of biases in the data.

5. The method of claim 4 further comprising using the data to determine an optimum calibration frequency for the instrument.

6. The method of claim 5 wherein an optimum calibration frequency for the instrument is determined by:
   (k) treating every xth data point in the data obtained in step (a) as a calibration point, wherein x is an integer greater than 1;
   (l) calculating the Euclidean distance for each value of x;
   (m) picking different values for x and repeating steps (k) and (l);
   (o) plotting the value of x vs. the calculated Euclidean distance; and
   (p) selecting an optimum calibration frequency from a region of values for x which produces relatively small Euclidean distances.

7. The method of claim 6 wherein an optimum calibration frequency is determined by the value for x which produces the smallest Euclidean distance.

8. A method for determining an optimum calibration frequency for an analytical instrument comprising:
   (a) obtaining a set of data from a series of replicate analyses by the instrument;
   (b) obtaining a series of random number sets, each set having a similar number of elements as the set of data obtained in step (a);
   (c) performing a Fast Fourier Transform on each of the sets in steps (a) and (b), thereby generating secondary spectra;
   (d) using a pattern recognition technique to determine how different the secondary spectrum corresponding to the data obtained in step (a) is from the distribution of the secondary spectra corresponding to the random number sets generated in step (b);
   (e) treating every xth element in the set of multivariate data obtained in step (a) as a calibration point and repeating step (d), where x is an integer greater than one;
   (f) repeating step e for a number of values for x; and (g) selecting an optimum calibration frequency for the instrument from a range of values for x which produces a relatively small difference between the secondary spectrum corresponding to the data obtained in step (a) and the distribution of secondary spectra corresponding to the random number sets generated in step (b).

9. The method of claim 8 wherein step (d) comprises:

plotting the area under a first portion of the secondary spectrum versus the area under a second portion of the secondary spectrum for each of the secondary spectra generated in step (c); and determining the Euclidean distance from the point in the plot corresponding to the set of data obtained in step (a) to the center of the distribution of points in the plot corresponding to the random number sets generated in step (b).

10. The method of claim 9 wherein the area under the first quarter of the secondary spectrum is plotted against the area under the first half of the secondary spectrum for each of the secondary spectra generated in step (c).

11. The method of claim 10 wherein the optimum calibration frequency is determined to be the value of x which produces the minimum difference between the secondary spectrum corresponding to the data obtained in step (a) and the distribution of secondary spectra corresponding to the random number sets generated in step (b).

12. A method of operating an analytical instrument comprising:

calibrating the instrument using known standards so that the response of the instrument can be correlated to a physical property of unknown sample;

analyzing a series of unknown samples;

recalibrating the instrument at an optimum calibration frequency, wherein said optimum calibration frequency is determined by (a) obtaining a set of data from a series of replicate analyses by the instrument;

(b) obtaining a series of random number sets, each set having a similar number of elements as the set of data obtained in step (a);

(c) performing a Fourier Transform on each of the sets in steps (a) and (b), thereby generating secondary spectra;

(d) using a pattern recognition technique to determine how different the secondary spectrum corresponding to the data obtained in step (a) is from the distribution of the secondary spectra corresponding to the random number sets generated in step (b);

(e) treating every ith element in the set of multivariate data obtained in step (a) as a calibration point and repeating step (d), where i is an integer greater than one;

(f) repeating step e for a number of values for i; and (g) selecting as an optimum calibration frequency for the instrument, a value of i from a range of values for i which produces a relatively small difference between the secondary spectrum corresponding to the data obtained in step (a) and the distribution of secondary spectra corresponding to the random number sets generated in step (b).

13. The method of claim 12 wherein step (d) comprises:

plotting the area under a first portion of the secondary spectrum versus the area under a second portion of the secondary spectrum for each of the secondary spectra generated in step (c); and determining the Euclidean distance from the point in the plot corresponding to the set of data obtained in step (a) to the center of the distribution of points in the plot corresponding to the random number sets generated in step (b).

14. The method of claim 13 wherein the area under the first quarter of the secondary spectrum is plotted against the area under the first half of the secondary spectrum for each of the secondary spectra generated in step (c).

15. The method of claim 14 wherein the optimum calibration frequency is determined to be the value of i which produces the minimum difference between the secondary spectrum corresponding to the data obtained in step (a) and the distribution of secondary spectra corresponding to the random number sets generated in step (b).

16. The method of claim 14 where the Fourier Transforms performed in step (c) are Fast Fourier Transforms.

* * * * *